US006235304B1

(12) United States Patent
Patterson

(10) Patent No.: US 6,235,304 B1
(45) Date of Patent: May 22, 2001

(54) METHOD OF INHIBITION OF HIV REPLICATION BY LEUKEMIA INHIBITORY FACTOR

(76) Inventor: Bruce K. Patterson, 211 W. St. Paul, Apt. 3, Chicago, IL (US) 60614

(*) Notice: Subject to any disclaimer, the term of this patent is extended or adjusted under 35 U.S.C. 154(b) by 0 days.

(21) Appl. No.: 09/443,984

(22) Filed: Nov. 19, 1999

(51) Int. Cl.[7] .............. A61F 2/02; A61F 13/02; A61K 9/48; A61K 9/20

(52) U.S. Cl. .............. 424/423; 424/434; 424/435; 424/443; 424/451; 424/464

(58) Field of Search .............. 424/423, 434, 424/435, 451, 464, 443

(56) References Cited

U.S. PATENT DOCUMENTS 5,837,241 * 11/1998 Ferrara .

* cited by examiner

*Primary Examiner*—Carlos A. Azpuru
(74) *Attorney, Agent, or Firm*—Niro, Scavone, Haller & Niro

(57) ABSTRACT

The present invention concerns a method for inhibiting HIV replication in a cell by binding Leukemia Inhibitory Factors ("LIF") LIF to its receptor in a cell to inhibit HIV replication within the cell. In addition, the present invention concerns a method for preventing uninfected individuals from infection with HIV by administering a dosage of LIF to prevent establishment of HIV infection. The present invention also provides a method of treating HIV infected individuals by administering a dosage of LIF to prevent disease progression.

15 Claims, 1 Drawing Sheet

METHOD OF INHIBITION OF HIV REPLICATION BY LEUKEMIA INHIBITORY FACTOR

BACKGROUND OF THE INVENTION

The invention relates to a treatment for reducing and/or preventing HIV from infecting cells. More specifically, the invention involves preventing the HIV virus from replicating by using Leukemia Inhibitory Factors ("LIF") to bind with its own specific receptors on T-lymphocytes or monocyte derived macrophages to prevent HIV replication.

SUMMARY OF THE INVENTION

Although the discovery of tropism specific HIV entry inhibitors began with Beta-chemokines, other factors with more global inhibitory function such as CAF (a CD8 derived antiviral factor)have been extensively studied but not unequivocally identified. The placenta remains an organ of intense study because vertical HIV transmission occurs in only 14–40% of untreated pregnancies despite exchange of blood between mother and fetus. A strong type 2 cytokine milieu (IL-4, IL-10) has been found in placentas from non-transmitting placentas that is significantly reduced in transmitting placentas. Associated with the type 2 cytokine response, it has not been found that non-transmitting placentas produce high levels of leukemia inhibitory factor (LIF). Thus, it has been determined that LIF is a potent inhibitor of HIV production with laboratory and primary isolates of HIV. Consequently, it has been found that LIF is involved in inhibition of both replication and vertical HIV transmission. As such, LIF may be used as a systemic treatment of infected individuals.

DESCRIPTION OF THE PREFERRED EMBODIMENTS

Figure 1:
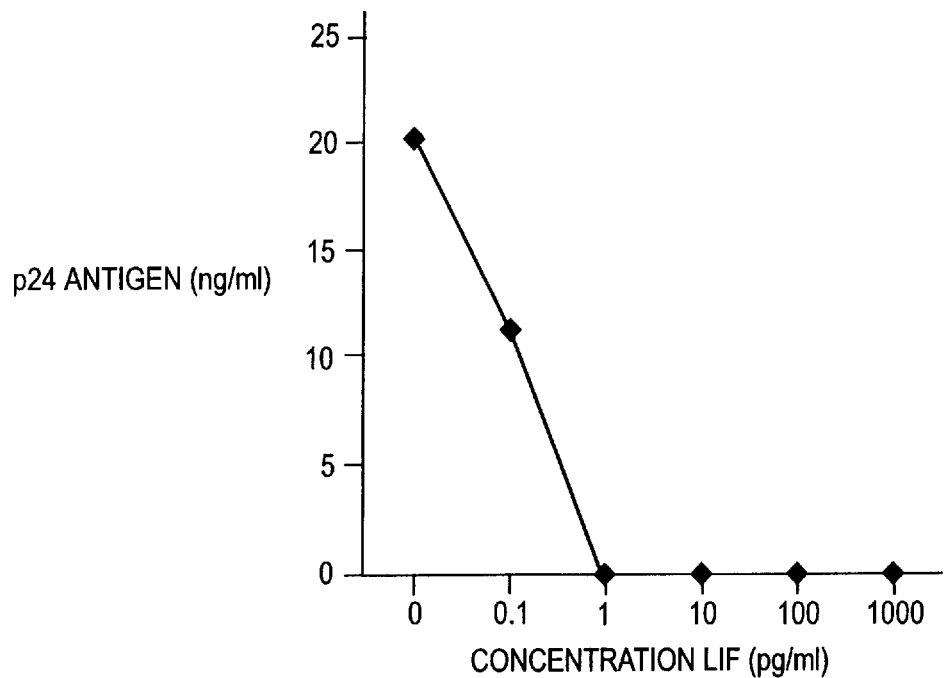
FIG. 1 shows the relationship between LIF concentration and fraction of virus produced by untreated controls infected with an HIV isolate that uses the CXCR4 receptor of a cell.

Set forth below is a description of what are currently believed to be the preferred embodiments or best examples of the invention claimed. Future and present alternatives and modifications to the preferred embodiments are contemplated. Any alternates or modifications in which insubstantial changes in function, in purpose, in structure or in result are intended to be covered by the claims of this patent.

In the absence of antiretroviral therapy 14%–40% of HIV infected women transmit HIV to their infants indicating that the placenta may play a protective role in vertical transmission. To study placenta derived factors that may contribute to protection, extensively washed, fresh or snap frozen placentas were obtained from six non-transmitting women and five transmitting women naive to antiretroviral therapy during their pregnancy and placentas from 3 HIV seronegative women. To identify blocks to HIV penetration or replication in placentas, total DNA or RNA from these placentas was applied to real time quantitative PCR or RTPCR gene panels consisting of HIV gag DNA, HIV gag mRNA, type 1, type 2, and inflammatory cytokines, chemokines, chemokine receptors, and LIF. Expression of HIV gag mRNA was found in 4 of 5 (80%) of term transmitting placentas (TT) and only 2 of 13 term non-transmitting placentas (15%). The average number of HIV mRNA copies in the TT placentas was 510/100,000 cells and the average number of copies of HIV mRNA in TNT placentas was less than the sensitivity of the assay which is 20 copies/100,000 cells. No significant difference was found in the number of placentas containing HIV DNA as HIV DNA was detected in 5 of 5 TT placentas (100%) and in 8 of 10 (80%) of TNT placentas, respectively. The average number of HIV DNA copies in TT placentas was 29.7 copies per 100,000 cells and the average number of copies in TNT placentas was 17.9 copies per 100,000 cells (p=NS). These results indicate that TNT placentas inhibit HIV replication better than TT placentas without significantly affecting the level of infected cells.

Cytokines have been shown to either increase or decrease HIV replication and the placenta is known to produce a multitude of type 1, type 2, and inflammatory cytokines. To determine if the expression pattern or quantity of cytokine expression might explain the significant difference in HIV gene expression in transmitting and non-transmitting placentas, cytokine message and protein in tissue sections were quantified by quantitative real time RTPCR and assisted computerized image analysis. There was a statistically significant elevation of type 2 cytokine (IL-4, IL-10) mRNA and protein expression relative to type 1 cytokine (IL-2) expression in placental tissue from non-transmitting placentas ($p<0.02$). In contrast, transmitting placentas showed significantly higher incidences of type 1 cytokine expression both at the mRNA and protein level ($p<0.05$) while type 2 cytokines were significantly upregulated in non-transmitting placentas compared to transmitting placentas ($p<0.01$). This type 2 cytokine upregulation did not correlate with superimposed chorioamnionitis, villitis, or vasculitis in any of the placentas.

To determine if LIF expression in HIV infected placentas followed the same cytokine regulation pattern as in uninfected placentas, I quantified LIF and mRNA and protein in all placentas. LIF mRNA was significantly upregulated in TNT placentas compared to TT placentas while quantification of LIF protein expression paralleled the mRNA expression. LIF mRNA and protein expression did not significantly differ from the production in normal placentas. The defective production of LIF in the TT placentas may explain the increase in spontaneous abortion in a certain population of HIV infected women with placental cytokine dysregulation.

Figure 2:
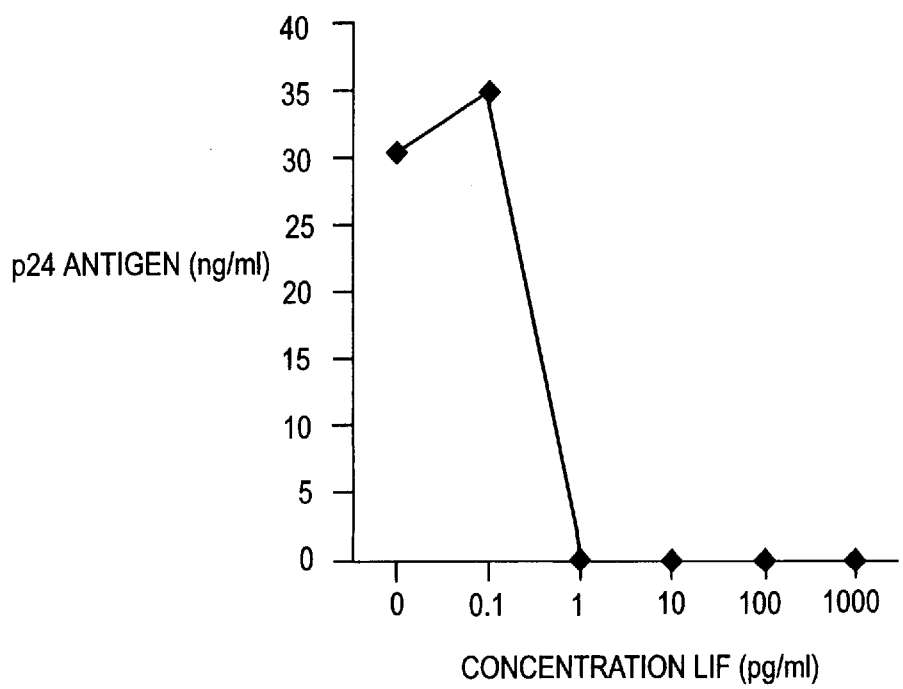
FIG. 2 shows the relationship between LIF concentration and fraction of virus produced by untreated controls infected with an HIV isolate that uses the CCR5 receptor of a cell.

The effects of IL-4 and IL-10 on HIV infection and replication are well established. To test the effects of LIF on HIV, dose dependent inhibition experiments with a 4-log range of LIF concentrations were performed from 0.1 pg/ml to 100 pg/ml. LIF inhibited the CCR5-using (R5) HIV Bal, the CXCR4-using (X4) HIV Lai, and the dual tropic (R5X4) HIV-1 ME46 with an IC50 of 0.5 pg/ml. Potent inhibition of HIV replication was detected in both T-lymphocytes and monocyte derived macrophages using simultaneous immunophenotyping/ultra sensitive in situ hybridization and flow cytometry. As shown in FIGS. 1 and 2, 100% reduction of virus production may be achieved through use of LIF. This demonstrates that LIF treatment may be used to inhibit the replication of the HIV virus in both infected and uninfected cells. First, LIF may be used as a systemic immune-based therapy for all HIV infected individuals by inhibiting the further replication of the virus in the host cells. This may be accomplished by inoculating and individual with LIF. Second, LIF may be used to prevent infection with the HIV virus through inoculation with LIF prior to exposure to the HIV virus. LIF is particularly suitable for use in human since it is a protein that is naturally found in humans.

Untreated controls infected with all isolates demonstrated high levels of both early and late reverse transcripts. The data suggest that the anti-viral activity of LIF takes place prior to reverse transcription; an activity that is distinct from CAF since CAF does not affect reverse transcription or proviral integration.

Infection of peripheral white blood cells from uninfected individuals were treated. A TCID50 of: 1000 for HIV Bal, 10,000 for HIV Lai, and 1000 for HIV ME46 was used to infect 107 PHA-stimulated peripheral blood mononuclear cells. The concentrations of recombinant, ultrapure (>99%) leukemia inhibitory factor were 0.01 pg/mL, 0.05 pg/mL, 1.0 pg/mL, and 10 pg/mL. All strains were tested in quadruplicate wells in three separate experiments. To correlate the replication endpoint concentration with a formal percent inhibitory concentration, we obtained that absolute p24 antigen content for each drug concentration. The concentration of drug that reduced the p24 antigen value of the control well by 50% (IC50) was calculated using non-parametric regression analysis and was found to be 0.5 pg/ml for all HIV isolates tested as shown in FIGS. 1 and 2. As also shown, LIF concentration at about 1 pg/ml show no viral replication.

Based upon the above, complete HIV replication in a host may be acheived by attaining LIF concentrations in blood or other tissues at about 1 pg/ml, depending bioavailability. This concentration is particularly useful since it is approximately 1000 fold less than other known HIV inhibitors such as RANTES, MIP-1alpha, and/or MIP-1beta, among others.

Dosages of LIF may be admisinstered in a number of ways known to those of skill in the art. For example, LIF may be administered by injection, orally, topically, mucosally, and in other ways. LIF has already proven to be safely administered to research animals to promote production of cells from the bone marrow. Recombinant LIF was obtained from Phar Mingen.

While the invention has been described with reference to the preferred embodiments thereof, it will be appreciated that numerous variations, modifications, and alternate embodiments are possible, and accordingly, all such variations, modifications, and alternate embodiments are to be regarded as being within the spirit and scope of the invention.

What is claimed is:

1. A method for inhibiting HIV replication in a cell comprising:
    binding LIF to its receptor in a cell to inhibit HIV replication within said cell.
2. The method of claim 1 wherein said LIF inhibits an HIV isolate using a CXCR4 receptor of said cell.
3. The method of claim 1 wherein said LIF inhibits an HIV isolate using a CCR5 receptor on said cell.
4. The method of claim 1 wherein said LIF inhibits an HIV isolate using both CCR5 and CXCR4 receptors of said cell.
5. The method of claim 1 wherein HIV replication is prevented in a white blood cell.
6. A method for preventing uninffected individuals from infection with HIV comprising:
    administering a dosage of LIF to prevent establishment of HIV infection.
7. The method of claim 6 wherein said dosage is delivered by injection.
8. The method of claim 6 wherein said dosage is delivered orally.
9. The method of claim 6 wherein said dosage is delivered topically.
10. The method of claim 6 wherein said dosages is delivered mucosally.
11. A method of treating HIV infected individuals comprising:
    administering a dosage of LIF to prevent disease progression.
12. The method of claim 11 wherein said dosage is delivered by injection.
13. The method of claim 11 wherein said dosage is delivered orally.
14. The method of claim 11 wherein said dosage is delivered topically.
15. The method of claim 11 wherein said dosages is delivered mucosally.

* * * * *